United States Patent
Volsky

(10) Patent No.: US 12,403,003 B1
(45) Date of Patent: Sep. 2, 2025

(54) TYMPANIC MEMBRANE PATCH AND LOADING VEHICLE

(71) Applicant: Peter G. Volsky, Virginia Beach, VA (US)

(72) Inventor: Peter G. Volsky, Virginia Beach, VA (US)

( * ) Notice: Subject to any disclaimer, the term of this patent is extended or adjusted under 35 U.S.C. 154(b) by 668 days.

(21) Appl. No.: 17/466,868

(22) Filed: Sep. 3, 2021

Related U.S. Application Data

(60) Provisional application No. 63/075,156, filed on Sep. 6, 2020.

(51) Int. Cl.
| | |
|---|---|
| *A61F 2/18* | (2006.01) |
| *A61F 11/00* | (2022.01) |
| *A61L 31/14* | (2006.01) |

(52) U.S. Cl.
CPC ............... *A61F 2/18* (2013.01); *A61F 11/00* (2013.01); *A61L 31/145* (2013.01); *A61L 31/146* (2013.01); *A61F 2002/183* (2013.01); *A61F 2230/0004* (2013.01); *A61F 2250/0069* (2013.01); *A61L 2430/14* (2013.01)

(58) Field of Classification Search
CPC ...... A61F 2/18; A61F 11/00; A61F 2002/183; A61F 2230/0004; A61F 2250/0069; A61L 2430/14; A61L 31/145; A61L 31/146; A61K 9/0046
See application file for complete search history.

(56) References Cited

U.S. PATENT DOCUMENTS

| | | | | |
|---|---|---|---|---|
| 5,259,032 | A * | 11/1993 | Perkins ................ | H04R 25/554 |
| | | | | 381/328 |
| 5,954,682 | A * | 9/1999 | Petrus ..................... | A61F 13/38 |
| | | | | 604/11 |
| 7,955,249 | B2 * | 6/2011 | Perkins ................ | H04R 23/008 |
| | | | | 600/25 |
| 8,858,419 | B2 * | 10/2014 | Puria .................... | H04R 25/606 |
| | | | | 607/57 |
| 8,886,280 | B2 | 11/2014 | Kartush | |
| 9,730,789 | B2 | 8/2017 | Kartush et al. | |
| 10,687,937 | B2 | 6/2020 | Kartush | |
| 2004/0071494 | A1 * | 4/2004 | Staniforth ............. | A45D 40/26 |
| | | | | 401/262 |
| 2010/0063376 | A1 | 3/2010 | Kartush | |
| 2010/0145178 | A1 | 6/2010 | Kartush | |
| 2010/0317956 | A1 | 12/2010 | Kartush | |
| 2015/0272728 | A1 | 10/2015 | Kartush et al. | |

(Continued)

OTHER PUBLICATIONS

Gupta et al "To Study the Association of the Size and Site of Tympanic Membrane Perforation with the Degree of Hearing Loss" Indian J Otolaryngol Head Neck Surg (Nov. 2019) 71(Suppl 2):S1047-S1052. (Year: 2019).*

(Continued)

*Primary Examiner* — Melanie R Tyson
*Assistant Examiner* — Rebecca Lynee Zimmerman
(74) *Attorney, Agent, or Firm* — Keusey & Associates, P.C.

(57) ABSTRACT

An apparatus for contacting a tympanic membrane fashioned as a removable non-resorbable patch. The patch has an oval periphery and a central portion with a proximal surface contoured to correspond in size and shape to a natural mammalian tympanic membrane. The proximal surface is adapted to contact a tympanic membrane or tympanic membrane tissue grafts.

15 Claims, 5 Drawing Sheets

(56) References Cited

U.S. PATENT DOCUMENTS

2018/0125641 A1   5/2018   Kartush
2018/0168501 A1   6/2018   Kartush

OTHER PUBLICATIONS

Bluestone CD et al, "How I do it"—otology and neurotology. A specific issue and its solution. Management of the patulous Eustachian tube. Laryngoscope. Jan. 1981;91(1):149-52 [online]. Retrieved from the Internet <URL: https://doi.org/10.1288/00005537-198101000-00023>. PMID: 7453462.

Dyer RK et al, The Patulous Eustachian Tube: Management Options. Otolaryngology—Head and Neck Surgery. 1991;105(6):832-835 [online]. Retrieved from the Internet <URL: https://doi.org/10.1177/019459989110500610>.

Kay DJ et al, Meta-analysis of tympanostomy tube sequelae. Otolaryngol Head Neck Surg. Apr. 2001;124(4):374-80 [online]. Retrieved from the Internet <URL: https://doi.org/10.1067/mhn.2001.113941>. PMID: 11283489.

Sato T et al, Trans-tympanic silicone plug insertion for chronic patulous Eustachian tube, Acta Oto-Laryngologica (2005), 125:11, 1158-1163, [online]. Retrieved from the Internet <URL: https://doi.org/10.1080/00016480510038167>.

Brace MD et al, Tympanic membrane manipulation to treat symptoms of patulous eustachian tube. Otol Neurotol. Aug. 2014;35(7):1201-6 [online]. Retrieved from the Internet <URL: https://doi.org/10.1097/MAO.0000000000000320>. PMID: 25111423.

Hussein AA et al, Surgical management of Patulous Eustachian tube: A systematic review. Laryngoscope. Sep. 2015;125(9):2193-8, [online]. Retrieved from the Internet <URL: https://doi.org/10.1002/lary.25168>. Epub Feb. 3, 2015. PMID: 25646902; PMCID: PMC4725712.

Wu C et al, Free vibration model and theoretical solution of the tympanic membrane, Computer Assisted Surgery (2016), 21:sup1, 61-68, [online]. Retrieved from the Internet <URL: https://doi.org/10.1080/24699322.2016.1240315>.

Kikuchi T et al, Effectiveness of Kobayashi plug for 252 ears with chronic patulous Eustachian tube. Acta Otolaryngol. Mar. 2017;137(3):253-258, [online]. Retrieved from the Internet <URL: https://doi.org/10.1080/00016489.2016.1231420>. Epub Sep. 26, 2016. PMID: 27666086.

Ward BK et al, Patulous Eustachian Tube Dysfunction: Patient Demographics and Comorbidities. Otol Neurotol. Oct. 2017;vol. 38; Issue 9; pp. 1362-1369, [online]. Retrieved from the Internet <URL: https://doi.org/10.1097/MAO.0000000000001543> PMID: 28796094.

Liao, David et al, Flat-panel CT Imaging of a Radiopaque Shim for Patulous Eustachian Tube Dysfunction, Otology & Neurotology: Mar. 2020—vol. 41—Issue 3—p. e412-e413, [online]. Retrieved from the Internet <URL: https//doi.org/10.1097/MAO.0000000000002503>.

Jack M. Kartush, Tympanic Membrane Patcher: A New Device to Close Tympanic Membrane Perforations in an Office Setting, Am J Otol, 21:615-620, 2000.

* cited by examiner

TYMPANIC MEMBRANE PATCH AND LOADING VEHICLE

CROSS-REFERENCE TO RELATED APPLICATION

This application claims the benefit under 35 U.S.C. § 119 (e) from U.S. Provisional Patent Application No. 63/075,156 entitled Tympanic Membrane Mass Loader filed on Sep. 6, 2020.

BACKGROUND OF THE INVENTION

1. Field of the Invention

The invention relates to a tympanic membrane patch and loading vehicle.

2. The Prior Art

Silicone has been used on wounds as a dressing and adjunctive therapy for epithelial healing for decades; applications have included flexible sheets and gels. Silicone and silastic sheets as well as patches containing these substances are also used in middle ear surgery.

The tympanic membrane's inner and outer layers are epithelial surfaces. The need arises to apply silicone to treat various epithelial disorders of the tympanic membrane and ear canal. Examples include tympanic membrane grafting (tympanoplasty and canaloplasty surgery), treatment of scars, and other epithelial disorders. The unique topology of the tympanic membrane renders it difficult to apply silicone sheets. An anatomically contoured tympanic membrane patch, fashioned from silicone, would allow precise positioning on the tympanic membrane.

Since the tympanic membrane and ear canal epithelium are in continuity, extensions or flanges of silicone sheet attached to the tympanic membrane patch could be placed in contact with ear canal skin.

A need remains for an effective surgical treatment that can be performed in the office setting (an awake patient, utilizing topical or local anesthesia) to relieve symptoms of PET dysfunction.

The tympanic membrane patch can be modified to include a housing for various applications, including masses, drug delivery devices, electronics. The use of masses, for example, renders the tympanic membrane patch a mass-loading device and would be applicable to the treatment of Patulous Eustachian Tube dysfunction (2015 Hussein, 1991 Dyer), similar to the manner described by mass-loading with putty (2014 Brace).

SUMMARY OF THE INVENTION

Accordingly, it is an object of the invention to provide a more effective treatment for various epithelial disorders.

It is a further object to provide a simplified surgical treatment that can be performed in an office setting.

It is another object to provide a tympanic membrane patch that functions as a mass-loading device.

It is a further object to provide tympanic membrane patches in varying sizes and thicknesses.

It is another object to provide a tympanic membrane patch with an internal cavity to receive an insert.

It is a further object to provide inserts in the form of weights of different masses It is another object to provide inserts in the form of electronic devices.

It is a further object to provide inserts in the form of drug delivery devices.

These and other related objects are achieved according to the invention by a cone or dome-shaped patch that functions as a tympanic membrane mass loader. The patch has an upper surface that matches the size and shape of the tympanic membrane. The patch has an oval base of varying sizes, where the major axis is about 6-11% larger than the minor axis.

The lower surface may have the same general concave depression as the upper surface, where the patch is of uniform thickness. The lower surface may have a shallower concave depression than the upper surface, where the patch has a gradually increasing thickness towards the middle of the device. The lower surface may be planar. The lower surface may extend outwardly below the plane of the oval. The lower surface may have a contour that is similar or different from the contour of the upper surface depending on the nature of the assisted healing intended. The patch is made from silicone or other biocompatible material.

The lower surface may be planar with the patch molded to form a solid silicone device. The patch includes a hollow compartment in the central portion of the device. Inserts are placed inside the compartment. Inserts comprise weights of different masses, custom selected for each patient. Inserts may alternatively comprise electronic devices or a drug delivery device.

The patch is sized and applied to the surface using microsurgical technique. The patch may be applied with or without antibiotic ointment. Alternatively a gel or adhesive may be applied.

The features of the invention include an apparatus for contacting a tympanic membrane. The apparatus includes a removable non-resorbable patch having a periphery with a closed curve oval geometry and a central portion having a proximal surface contoured to correspond in size and shape to a natural mammalian tympanic membrane. The proximal surface is adapted to contact a tympanic membrane or tympanic membrane tissue grafts.

The patch is made from a biocompatible flexible material. The proximal surface has a dome shape, and the patch includes a distal surface opposite the proximal surface. The proximal surface has a convex contoured shape with cross sectional lines approximating a hyperbolic curve and is adapted to contact the tympanic membrane to provide flexible support to assist healing thereof. A flange extends outwardly from the distal surface. The flange is made from a biocompatible material with a higher density than the biocompatible flexible material. The flange is adapted to be grasped by a surgical instrument for placement of the proximal surface in contact with the tympanic membrane. The patch is made of solid surgical grade silicone.

The central portion further includes a distal surface opposite the proximal surface, wherein the proximal surface has a maximum height $H_p$ measured from a plane disposed at an upper edge of the periphery, and wherein the distal surface has a maximum depth $D_d$ measured from a plane disposed at a lower edge of the periphery. The depth $D_d$ is less than or equal to the height $H_p$, and wherein the distal surface has a concave contoured shape. The periphery has a minor axis between 6 and 11 mm and a major axis between about 6 to 11% longer than the minor axis. The major axis is proportionally longer as the minor axis length increases. The depth $D_d$ is equal to the height $H_p$ whereby the central portion has a generally uniform thickness throughout. The depth $D_d$ is less than the height Hp whereby the central portion increases in thickness towards the middle of the patch.

The distal surface is generally flat whereby the central portion increases in thickness towards a middle of the patch. The distal surface has a maximum height Hd that extends beyond the lower edge of the periphery. The periphery extends radially with a uniform thickness. The thickness of the periphery decreases in a radially outward direction. The central portion includes one of an internal sealed pocket or an internal resealable pocket, and wherein the apparatus further includes an insert disposed in the internal pocket. The insert has a density greater than a density of the patch, and wherein the insert has a varying mass to adjust a damping effect on the tympanic membrane. The insert is a compound dispensing device and wherein the internal portion includes micro-channels extending from the pocket to the proximal surface to deliver a compound to the tympanic membrane or tympanic membrane tissue grafts. The insert is an electronic device to improve a patient's hearing.

The patch is made from a biocompatible material selected from the group consisting of silicone, fluoro-silicone, rubber, polyurethane, polyurethane derivatives, surgical grade polymers, a surgical grade flexible material, a surgical grade elastomeric material, an open cell elastomeric foam, a closed cell elastomeric foam and a hydrogel. A medical composition is applied to the proximal surface for contacting the tympanic membrane, wherein the medical composition is selected from the group consisting of an antibiotic, a healing ointment, a healing gel, a healing compound and a biocompatible releasable adhesive.

BRIEF DESCRIPTION OF THE DRAWINGS

The advantages, nature, and various additional features of the invention will appear more fully upon consideration of the illustrative embodiments now to be described in detail in connection with accompanying drawings. In the drawings wherein like reference numerals denote similar components throughout the views.

DETAILED DESCRIPTION OF THE PREFERRED EMBODIMENT

Silicone has been used on wounds as a dressing and adjunctive therapy for epithelial healing for decades; applications have included flexible sheets and gels. Silicone and silastic sheets as well as covers containing these substances are also used in middle ear surgery.

The invention relates to medical devices applicable to the practice of otolaryngology, specifically otology. Certain embodiments of the invention can relieve symptoms of "Patulous" Eustachian tube (PET) a benign, uncommon disorder of the middle ear. It is problematic for patients and otologists because neither a cure nor an optimal treatment exists.

Currently these conditions have been treated with limited success by manual trimming of putty (2014 Brace) and applying to the eardrum. The tympanic membrane has diameters of 8-9 mm by 8.5-10 mm and has an inverse conical shape. (2016 Wu). Other treatments manually trim silicone and apply it to the eardrum. Since the tympanic membrane and ear canal epithelium are in continuity, extensions or flanges of silicone sheet attached to the tympanic membrane patch could be placed in contact with ear canal skin.

According to an embodiment of the invention, an apparatus is provided for contacting a tympanic membrane. As show in FIGS. 1 and 2 the apparatus consists of a removable patch 20 made from a non-resorbable, flexible material. The patch has a general dome shape on its upper surface. The edge is formed as an oval periphery with a smooth rounded mound extending up from the periphery.

Figure 1:
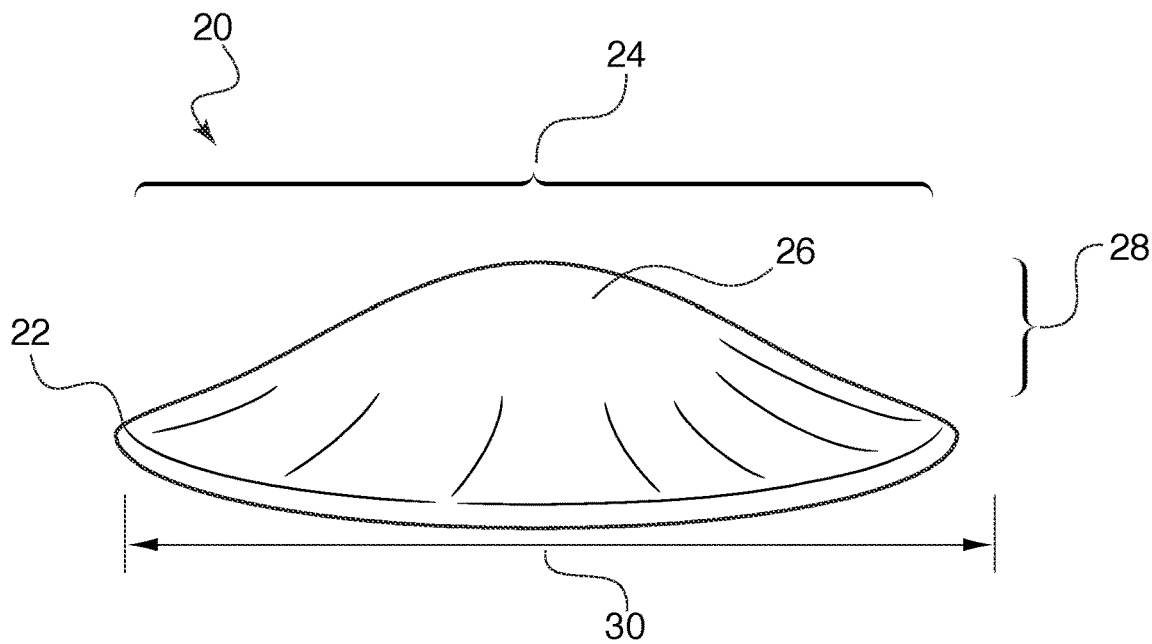
FIG. 1 is a front side elevational view of an embodiment of the tympanic membrane patch according to the invention.
Figure 2:
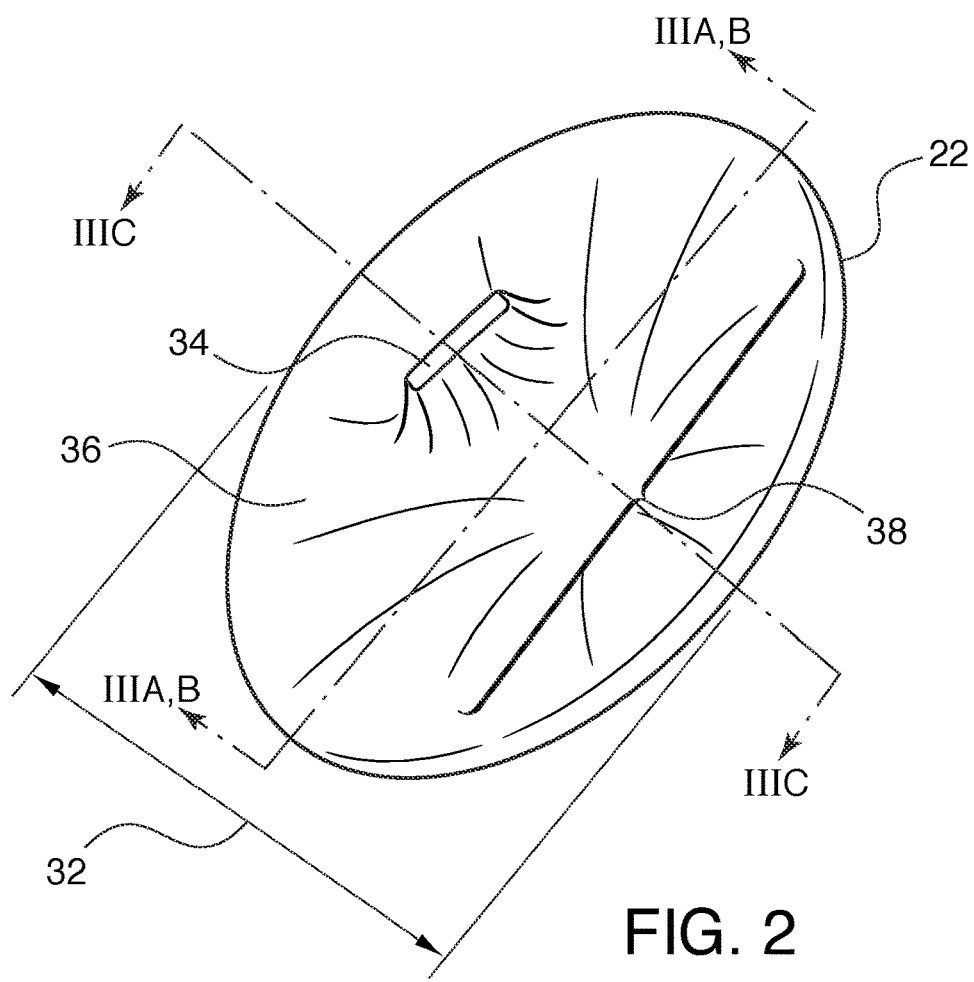
FIG. 2 is a bottom perspective view thereof.

The patch 20 features a periphery 22 that borders the device in an oval shape. The periphery 22 resides within a plane. FIG. 1 shows the proximal surface 26, while FIG. 2 shows the distal surface 36. Where proximal means nearest to, or facing, the tympanic membrane and where distal means farthest from, or facing away from, the tympanic membrane.

The proximal surface 26 has a top central portion 24 within periphery 22. The top central portion 24 has a convexly contoured shape 28. The distal surface 36 has a bottom central portion 38 within periphery 22. The bottom central portion 38 encompasses various shapes, as will be described more fully below. In one embodiment a flange 34 is provided, which functions as a handle to facilitate grasping of the patch and properly positioning it in contact with the tympanic membrane.

For any diameter extending from the near periphery to the far periphery across the central portion, the smooth rounded shape can be described as a regular, symmetrical, normal shallow curve. For example, with a 10 mm diameter, the height of the curve would be about 2-4 mm. In general, the height of the central portion is about 20-40% of the length of the diameter. The proximal surface follows a gentle curve rising from the near periphery, smoothly peaking and inverting to follow the gentle curve back to the far periphery. Across the major axis of symmetry, e.g. IIIA,B, the proximal surface may be a hyperbolic curve. Across the minor axis of symmetry, e.g. IIIC, the proximal surface may be a slightly steeper hyperbolic curve.

In colloquial terms the proximal surface is a dome-shape rising from an oval base. In mathematical terms, any diameter or line of symmetry across the proximal surface includes a hyperbolic curve projecting upwardly from a plane. More particularly, a hyperbolic curve equal to, or approximating, the curve shown in Graph 1, where y=sech x. Other lines across the proximal surface include an asymmetrical hyperbolic curve projecting upwardly from a plane.

The base of the tympanic membrane is oval shape with the major axis 32 being between about 6-11% larger than the minor axis 30. The periphery of the base lies in a single plane. Moving inwardly from the periphery, the membrane has a concave depression. The overall shape is referred to as an inverse conical shape.

The patch can be produced in a variety of sizes. At the smaller end of the spectrum, a patch would have a minor axis of about 6-8 mm and a major axis of 6.4-8.5 mm. In this instance the major axis is about 6% larger than the minor axis. At the larger end, a patch would have a minor axis of 9-11 mm and a major axis of 10-12.2 mm. In this instance the major axis is about 11% larger than the minor axis. One or more intermediate sized patches could be provided. As the minor axis increases from 6 mm to 11 mm the ratio to the major axis also increases linearly from 6% to 11%.

Figure 3A:
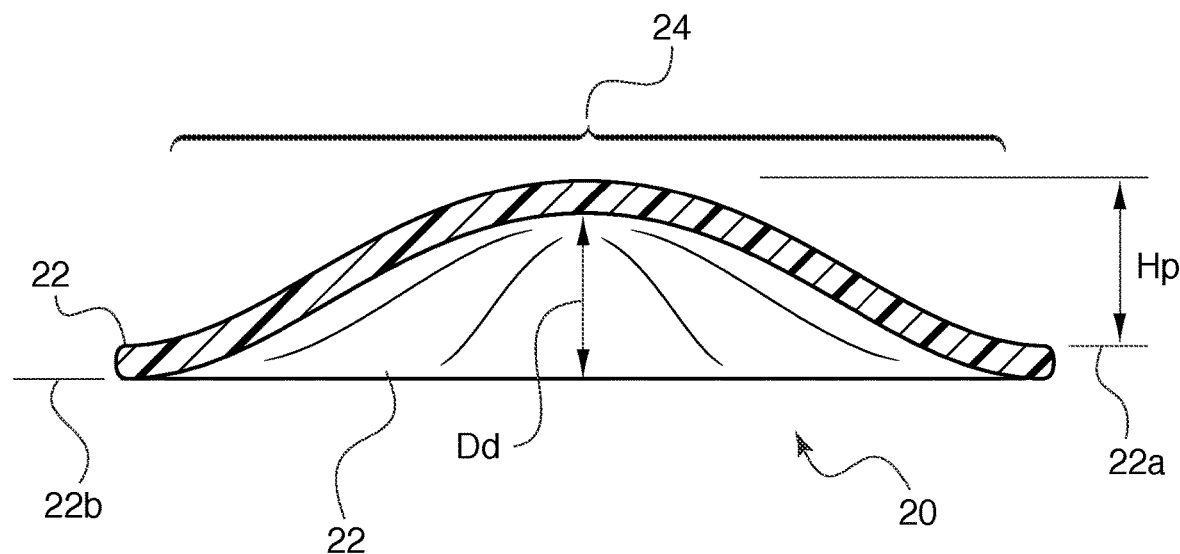
FIGS. 3A and 3B are cross-sectional views showing two embodiments of the patch's distal surface depth and height.

The patch is made from silicone or other biocompatible material. The patch may be molded as a solid silicone conical disc. The patch may be of uniform thickness ranging from less than a mm in thickness to greater than 1 mm in thickness. For uniformly thick patches, the lower surface has the same general shape as the upper surface. As can be seen in FIG. 3A, the Height of the proximal surface Hp is measured from the upper edge 22a of periphery 22 to the peak of top surface 24. The Depth of the distal surface Dd is measured from the lower edge 22b of periphery 22 to the peak of bottom central portion. For patches of uniform thickness Hp equals Dd for the central portions. The uniform thickness may be extended to the periphery, where the thickness is measured as the distance between upper edge 22a and lower edge 22b.

Figure 3B:
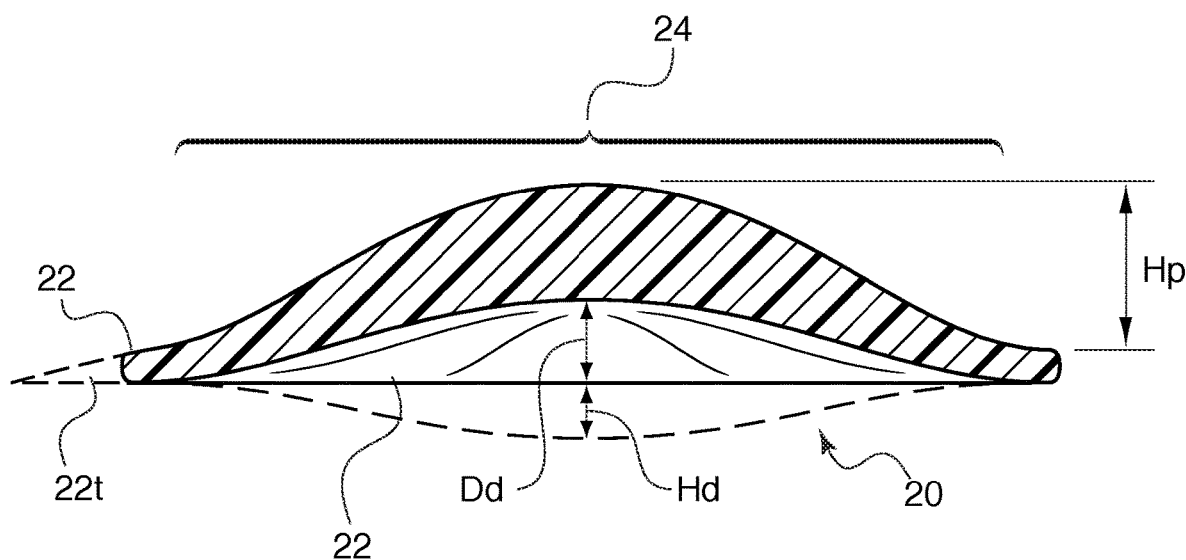

The patch may have varying thickness where the lower surface exhibits less concavity than the upper surface. For example, the thickness at the periphery could be 1 mm and gradually increasing to a thickness of 2 mm at the center of the patch. In one embodiment the lower surface is planar. In other words, the concavity is completely filled to provide a flat lower surface. In a further embodiment shown in FIG. 3B, the lower surface is also convex, extending down below the plane, that is a Height Hd extending beyond the lower plane. Such a device could be molded as a solid silicone patch. The periphery may taper down in any of the embodiments to a point, shown as a periphery tail 22t. As can be seen the distal surface may be configured in a variety of ways with varying contours, the particular selection of which is application specific.

Figure 3C:
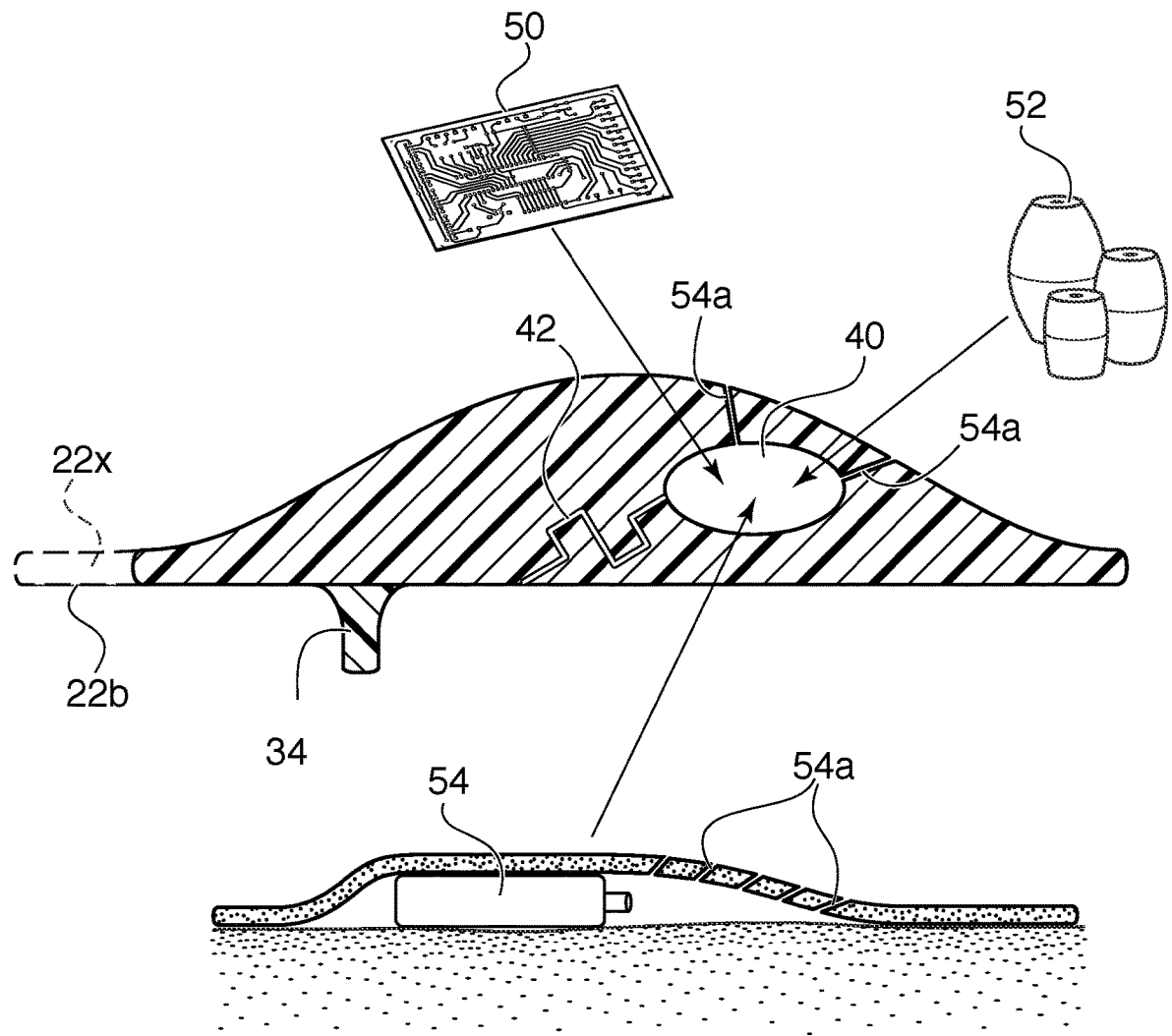
FIG. 3C is a cross-sectional view showing a further embodiment of the patch's distal surface being generally flat with optional pocket.

Alternatively, the central portion of the patch could be fitted with a hollow compartment or pocket for placement of inserts. As shown in FIG. 3C, a pocket 40 is accessible via a self-sealing access port, for example, a tongue and groove seal 42. Inserts would comprise electronic devices 50, weights 52 of various masses or drug delivery devices 54. Thus the inventive dome can be customized to load a particular mass for each patient, or provide different loads over the course of a healing process. The electronic devices could be hearing aids, sensors, medical monitors, or devices which record medical data and wirelessly report via a transponder. The drug delivery devices could dispense micro-fluidic amounts of lubricant, medication or antibiotics through micro-channels 54a to the tympanic membrane or tympanic membrane tissue grafts. Multiple devices may be placed within the pocket. The access port can be manipulated open and closed via the flange 34. The periphery may extend outwardly at a constant thickness in any of the embodiments, shown as a periphery extension 22x.

According to the invention a small dome-shaped patch, made from silicone, could be applied to the surface of the tympanic membrane or tympanic membrane tissue grafts. The tympanic membrane's inner and outer layers are epithelial surfaces. The application of biocompatible, flexible silicone can treat various epithelial disorders of the tympanic membrane and ear canal. Examples include tympanic membrane grafting (tympanoplasty and canaloplasty surgery), treatment of scars, and other epithelial disorders. The anatomically contoured tympanic membrane patch according to the invention featuring a bracket would allow convenient handling without touching the patch and facilitate precise positioning on the tympanic membrane. The advantages of this are that it is non-invasive and completely reversible. The silicone sitting on the ear canal skin and eardrum has low risk of injury.

Figure 4A:
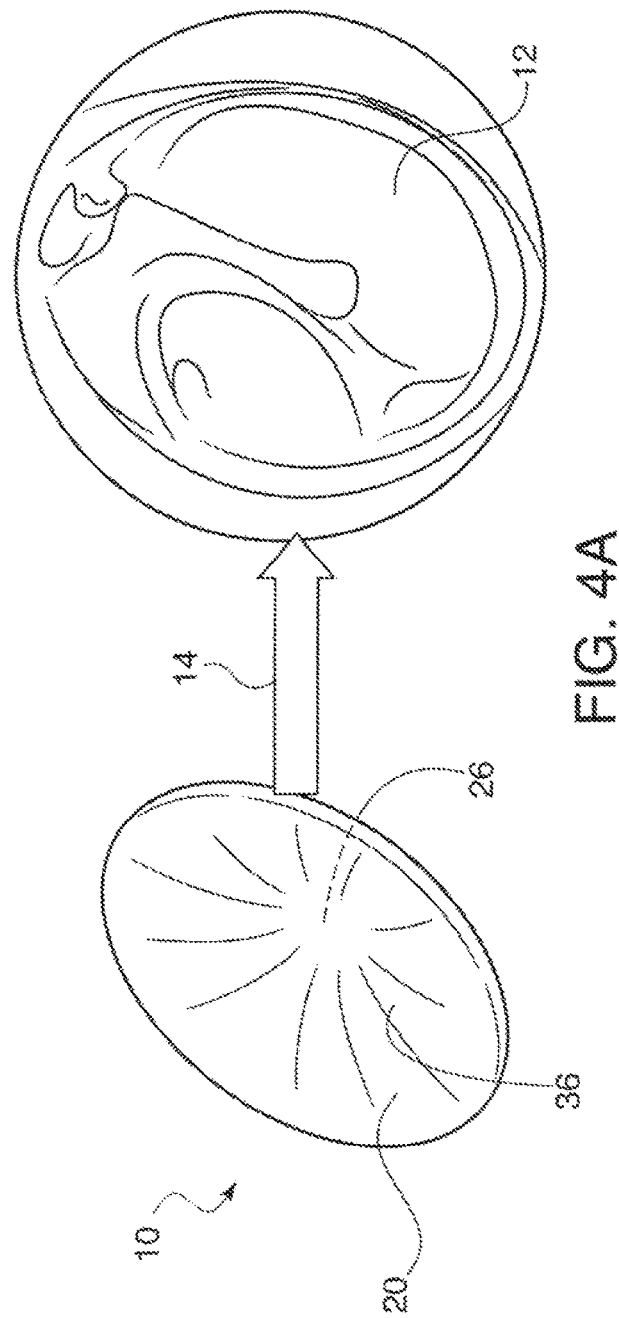
FIG. 4A is a diagram illustrating the patch relative to a tympanic membrane.

FIG. 4A shows an embodiment of the apparatus 10 according to the invention in relation to a tympanic membrane 12. The concave, distal surface 36 is visible, with the convex, proximal surface 26 facing the tympanic membrane. During a microsurgical technique, the convex, proximal surface 26 is brought into contact with the tympanic membrane 12 by inserting the patch through the ear canal until the proximal surface gently contacts the tympanic membrane as illustrated by arrow 14. The patch could be collapsed like an umbrella and guided through the ear canal. The patch could be directed into proper position by grasping the bracket, not shown in FIG. 4A for the sake of clarity.

Figure 4B:
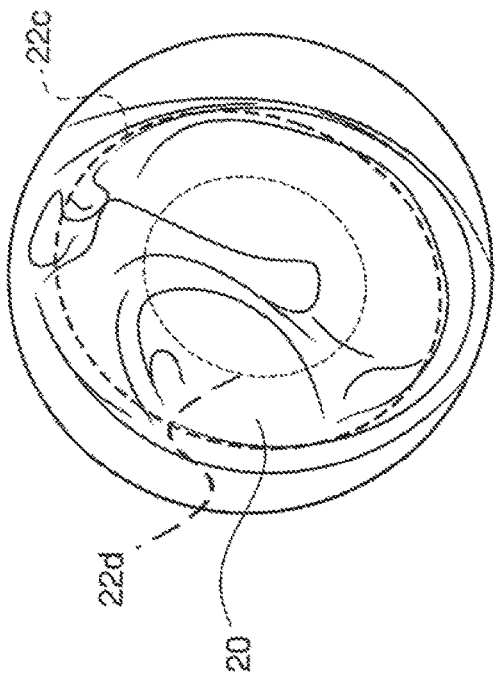
FIG. 4B shows the range of patch placement options on the tympanic membrane.
Figure 5:
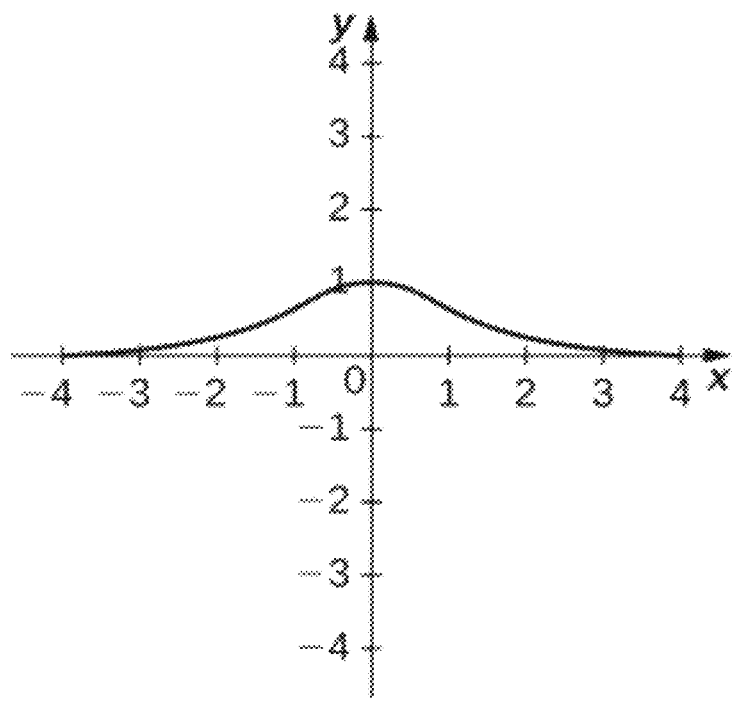
FIG. 5 is a graph showing one embodiment of the shape of the proximal surface.

FIG. 4B shows the periphery of patch 20 in dotted line once placed on the tympanic membrane. In this view, the patch is transparent for the sake of clarity. The outer dotted oval 22c represents the location of the periphery for a normal size patch. The inner dotted oval 22d represents the location of the periphery for a slightly smaller size patch. The patch can be provided in a variety of sizes, with the ovals 22c and 22d representing a range of locations to which the patch can be placed.

The inventive cone or dome functions as a tympanic membrane patch and loading device to assist healing. It has an upper surface that is configured to match the size and shape of the tympanic membrane. It is situated on the tympanic membrane for a variety of applications. One such application would provide the dome as a support surface to assist healing following tympanic membrane graft surgery. In this instance the patch functions as a support surface rather than a mass loading member. The cone could be used for either purpose in combination with application of gel, adhesive and/or antibiotics. In certain assisted healing applications, the ratio between the minor axis and the major axis of the periphery could be less than the ratio specified above. The patch could be used as a vehicle for a biologic covering on its proximal surface to promote tympanic membrane healing.

The patch can be manufactured by molding silicone, for example, injection molding silicone. The flange is ideally formed from a material that is denser than the patch material, for example a higher density silicone, or another biocompatible material. To form the pocket, a so-called insert molding process can be utilized. The insert would reside within the mold prior to injection of the silicone. The insert would extend from the lower edge 22b up in to the mold cavity. The insert would include a square-sawtooth blade terminating in a sphere. After molding, once the silicone is set, the patch could be pried off the insert, leaving a tongue and groove access port 42 to the pocket 40, as shown in FIG. 3C. The access port extends about one-quarter to one-half the diameter of the patch. The microchannels 54a would then be bored through the proximal surface to the pocket. Other manufacturing techniques familiar to those skilled in the art may be employed.

The silicone patch can be sized and applied to the surface of the tympanic membrane with or without antibiotic ointment. The patch can be placed using standard microsurgical techniques. It can also be removed at any time. Thus the patch can be removed to vary the internal weight, adjust the electronic device, replace the battery of the electronic device, or switch between different types of inserts.

Having described preferred embodiments for (which are intended to be illustrative and not limiting), it is noted that persons can make modifications and variations skilled in the art in light of the above teachings. The patch may have a variety of configurations including varying slopes and edge contours. The use of equivalent materials other than those specified is intended to be included within the scope of the invention. It is therefore to be understood that changes may be made in the particular embodiments of the invention disclosed which are within the scope and spirit of the invention as outlined by the appended claims. Having thus described the invention with the details and particularity required by the patent laws, the features intended to be protected by this application are as follows.

What is claimed is:

1. An apparatus for contacting a tympanic membrane or a tympanic membrane tissue graft comprising:
    a removable non-resorbable patch made from a biocompatible flexible material having:
        a periphery with a closed curve oval geometry;
        a central portion having a distal surface and a proximal surface contoured to correspond in size and shape to a natural mammalian tympanic membrane; and
        a flange extending outwardly from the distal surface made from a biocompatible material with a higher density than the biocompatible flexible material and wherein the flange is adapted to be grasped by a surgical instrument for placement, wherein the proximal surface is adapted to contact the tympanic membrane or the tympanic membrane tissue graft.

2. The apparatus of claim 1, wherein the biocompatible flexible material is solid surgical grade silicone.

3. The apparatus of claim 1, wherein the proximal surface has a dome shape, and wherein the distal surface is opposite the proximal surface.

4. The apparatus of claim 3, wherein the proximal surface has a maximum height Hp measured from a plane disposed at an upper edge of the periphery, and wherein the distal surface has a maximum depth Dd measured from a plane disposed at a lower edge of the periphery.

5. The apparatus of claim 4, wherein the depth Dd is less than or equal to the height Hp, and wherein the distal surface has a contoured shape.

6. The apparatus of claim 4, wherein depth Dd is equal to the height Hp whereby the central portion has a generally uniform thickness throughout.

7. The apparatus of claim 4, wherein the depth Dd is less than the height Hp whereby the central portion increases in thickness towards a middle of the patch.

8. The apparatus of claim 3, wherein the distal surface is generally flat whereby the central portion increases in thickness towards a middle of the patch.

9. The apparatus of claim 1, wherein the proximal surface has a convex shape approximating a hyperbolic curve and is adapted to contact the tympanic membrane or the tympanic membrane tissue graft to provide flexible support to assist healing thereof.

10. The apparatus of claim 1, wherein the flange extends perpendicularly outward from the distal surface.

11. The apparatus of claim 1, wherein the periphery has a minor axis between 6 and 11 mm and a major axis between about 6 to 11% longer than the minor axis and wherein the major axis is proportionally longer as the minor axis length increases.

12. The apparatus of claim 1, wherein the periphery extends radially outwardly with a uniform thickness.

13. The apparatus of claim 1, wherein the biocompatible flexible material is selected from the group consisting of silicone, fluoro-silicone, rubber, polyurethane, polyurethane derivatives, surgical grade polymers, a surgical grade flexible material, a surgical grade elastomeric material, an open cell elastomeric foam, a closed cell elastomeric foam and a hydrogel.

14. The apparatus of claim 1, wherein the proximal surface is adapted to receive a healing compound, wherein the healing compound is selected from the group consisting of an antibiotic, a healing ointment and a healing gel.

15. An apparatus for contacting a tympanic membrane or a tympanic membrane tissue graft comprising:
    a removable non-resorbable patch made from a biocompatible flexible material having:
        a periphery with a closed curve oval geometry;
        a central portion having a proximal surface contoured to correspond in size and shape to a natural mammalian tympanic membrane, and a distal surface opposite the proximal surface; and
        a flange made from a biocompatible material with a higher density than the biocompatible flexible material extending outwardly from the distal surface, wherein the flange is adapted to be grasped by a surgical instrument for placement,
    wherein the proximal surface has a convex shape approximating a hyperbolic curve and is adapted to contact the tympanic membrane or the tympanic membrane tissue graft to provide flexible support to assist healing thereof.

* * * * *